(12) United States Patent
Maleev et al.

(10) Patent No.: US 6,605,440 B2
(45) Date of Patent: *Aug. 12, 2003

(54) METHOD FOR DETERMINING ANALYTE LEVEL

(75) Inventors: Alexander Michaelovich Maleev, Moscow (RU); Yevgeney Borisovich Bablyuk, Moscow (RU); Ivan Alexandrovich Kochetov, Moscow (RU); Alexandr Sergeivich Parfenov, Moscow (RU); Yury Michaelovich Lopukhin, Moscow (RU); Alxandr B. Rabovski, Salt Lake City, UT (US)

(73) Assignee: IMI International Medical Innovations Inc., Mississauga (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 263 days.

(21) Appl. No.: 08/849,252

(22) PCT Filed: Dec. 14, 1995

(86) PCT No.: PCT/CA95/00698

§ 371 (c)(1),
(2), (4) Date: Sep. 16, 1997

(87) PCT Pub. No.: WO96/18898

PCT Pub. Date: Jun. 20, 1996

(65) Prior Publication Data

US 2001/0007773 A1 Jul. 12, 2001

(30) Foreign Application Priority Data

Dec. 16, 1994 (RU) .............................................. 94044169

(51) Int. Cl.⁷ ........................ G01N 33/00; G01N 33/53; G01N 31/00; C12Q 1/60
(52) U.S. Cl. ...................... 435/7.1; 435/7.9; 435/287.1; 435/287.2; 435/287.7; 435/287.8; 435/287.9; 435/805; 435/810; 435/970; 435/11; 435/4; 435/20; 436/164; 436/169; 436/170; 436/518; 436/805; 422/56; 422/57; 422/58; 23/253; 430/217
(58) Field of Search ........................... 435/7.1, 11, 7.9, 435/4, 20, 287.1, 287.2, 287.7, 287.8, 287.9, 805, 810, 970; 195/103.5, 99; 422/56, 57, 58; 23/253; 430/217; 436/164, 169, 170, 518, 805

(56) References Cited

U.S. PATENT DOCUMENTS

| | | | | |
|---|---|---|---|---|
| 3,983,005 A | * | 9/1976 | Goodhue et al. | 195/103.5 |
| 3,992,158 A | * | 11/1976 | Przybylowicz et al. | 23/253 |
| 4,089,747 A | * | 5/1978 | Bruschi | 195/99 |
| 4,281,061 A | * | 7/1981 | Zuk et al. | 435/7 |
| 4,587,100 A | * | 5/1986 | Amano et al. | 422/56 |
| 4,732,736 A | * | 3/1988 | Kobayashi et al. | 422/56 |
| 4,826,761 A | | 5/1989 | Arai et al. | 435/11 |
| 4,876,207 A | * | 10/1989 | Mack, II et al. | 436/135 |
| 5,155,024 A | * | 10/1992 | Eikenberry | 435/7.9 |
| 5,156,948 A | * | 10/1992 | Christensen et al. | 435/5 |
| 5,489,510 A | | 2/1996 | Lopukhin et al. | 435/7.1 |
| 5,587,295 A | | 12/1996 | Lopukhin et al. | 435/11 |

FOREIGN PATENT DOCUMENTS

| | | | | |
|---|---|---|---|---|
| EP | 60158 | 9/1982 | | C12Q/1/28 |
| EP | 130520 | 1/1985 | | C12Q/1/28 |
| EP | 272578 | 6/1988 | | C12Q/1/60 |
| EP | 285998 | 10/1988 | | C12Q/1/32 |
| EP | 338189 | 10/1989 | | G01N/33/92 |
| EP | A-0 338 189 | * | 10/1989 | G01N/33/92 |

* cited by examiner

*Primary Examiner*—Long V. Le
*Assistant Examiner*—Lisa V. Cook
(74) *Attorney, Agent, or Firm*—Foley & Lardner

(57) ABSTRACT

A multilayer analytical element for determining a level of an analyte on a substrate and adapted for use with hydrogen peroxide and an affinity-enzymatic compound of formula A-C-B, wherein A is a detecting agent having affinity for the analyte, B is an enzymatic visualizing agent consisting of peroxidase and C is a binding agent linking the detecting and visualizing agents together. The multilayer analytical element of the invention comprises a solid support and a hydrophilic layer thereon, the hydrophilic layer being formed of gelatin, polyvinyl alcohol or a mixture thereof and containing a developing agent and a hydrophobic color-producing agent in a total amount of 5 to 30 weight %, the developing agent and the color-producing agent being present in a weight ratio of 1:0.3 to 1:3.0. The developing agent is capable of undergoing oxidation by the hydrogen peroxide in the presence of the peroxidase bound via the binding and detecting agents to the analyte on the substrate, whereby the developing agent in oxidized form reacts with the color-producing agent to form a colored product having a color indicative of the level of analyte.

12 Claims, No Drawings

METHOD FOR DETERMINING ANALYTE LEVEL

This application is a §371 national stage of PCT CA95/00698 filed Dec. 14, 1995.

BACKGROUND OF THE INVENTION

The present invention relates to improvements in the field of material analysis. More particularly, the invention relates to a multilayer analytical element for measuring the level of cholesterol on human skin or other animal tissue.

USSR Author Certificate No. 1,054,784 describes an analytical element which is used in thin-layer chromatography of lipids and which consists of a support (such as a glass plate), having thereon a layer of an adsorbing material such as a mixture of silica gel, gypsum, ammonium sulfate and copper acetate. Such an analytical element is not suitable for measuring cholesterol on human skin.

USSR Author Certificate No. 1,495,378 describes a two-layer analytical element which comprises a support such as a polyethylene film and a layer of gelatin with immobilized oxidase as an enzyme. The element changes color when amines or aqueous solutions thereof contact the gelatin layer. Such an analytical element is also not suitable for measuring cholesterol on human skin.

Canadian Patent No. 1,335,968 describes a method of measuring cholesterol by contacting the skin or another cholesterol-containing surface with an affinity-enzymatic compound of the general formula A-C-B, wherein A is a detecting agent having affinity for cholesterol, B is an enzymatic visualizing agent capable of reacting with a color-producing agent to form a colored product, and C is a binding agent linking the detecting and visualizing agents together. The presence of cholesterol is determined by a change of color of the color-producing agent. Such a method has drawbacks in that the solutions and colored reaction product are not sufficiently stable and that at low cholesterol levels the sensitivity and reproducibility are rather poor.

Due to the drawbacks associated with the above known analytical elements and with the above known method of measuring cholesterol, it is necessary to develop an analytical element combining the advantages of the known liquid-phase method for cholesterol assay and the convenience of practical application of multilayer analytical elements utilizing solid supports.

A multilayer analytical element has been proposed in U.S. Pat. No. 4,895,704, which comprises a water-impermeable light-transmitting solid support and a hydrophilic layer containing at least one reagent capable of reacting with a component of a sample to form a substance which can be detected by light radiation. The analytical element includes an additional layer containing light-scattering particles in an amount ensuring light transmittance in the range from 10 to 2.5%. Drawbacks to such a known multilayer analytical element are its non-suitability for measuring cholesterol levels on skin, low intensity of color reaction and high contrast of analytical effect at low levels of substance being assayed.

U.S. Pat. No. 4,826,761 discloses a multilayer analytical element for analysis of cholesterol contained in an aqueous liquid sample such as blood or other body fluids. Such an analytical element comprises a water-impermeable light-transmissive support, a hydrophilic layer and a spreading layer containing cholesterol esterase and cholesterol oxidase, superposed in this order. The analytical element further contains peroxidase and a coloring reagent composition which may be present in either the hydrophilic layer or spreading layer. As the coloring reagent composition, a combination of 4-aminoantipyrine or its derivative and 2-hydroxy-3,5-dichlorobenzene sulfonic acid is employed. The peroxidase oxidizes. 4-aminoantipyrine by utilising the hydrogen peroxide produced by the cholesterol reactions to couple with 2-hydroxy-3,5-dichlorobenzene sulfonic acid, thereby providing a color change or coloring in the multilayer analytical element. Since 4-aminoantipyrine acts as a color-producing agent and is a hydrophilic compound, it would be removed from the hydrophilic layer upon contacting the analytical element with the skin.

Published European Patent Application No. 60,518 discloses a fluorescent method for assaying hydrogen peroxide formed as a result of enzyme-catalysed reactions of certain substrates such as glucose and cholesterol. Example 4 refers to cholesterol which is determined in liquid phase by subjecting the cholesterol to the action of cholesterol oxidase to form hydrogen peroxide and quantitatively measuring the hydrogen peroxide thus formed by reacting the same with a hydrogen donor, peroxidase and a reagent composed of a moiety having a residue formed by removing one hydrogen from an active methylene group or an active methine group and a fluorescing moiety. The fluorescence emitted from the flurorescent material formed by the reaction is then measured. Reaction of the hydrogen donor (i.e., developing agent) with the reagent (i.e., color-producing agent) occurs in liquid phase, and not in solid phase.

Published European Patent Application No. 285,998 discloses a method for the determination of dehydrogenase or its substrate, and thus does not refer to the determination of cholesterol. All reactions are performed in liquid phase. The hydrogen peroxide formed by the dehydrogenase reaction is reacted with a peroxidase and a chromogen to form a dye and the dye is measured by spectrophotometry. The chromogens which are described in the publication and which may include 4-aminoantipyrine/aniline derivatives, 4-aminoanti-pyrine/phenol derivatives and benzothiazolinone hydrazone derivatives/aniline derivatives are all hydrophilic compounds.

SUMMARY OF THE INVENTION

It is therefore an object of the present invention to enhance the sensitivity, reproducibility and intensity of color reaction of analytical elements, to increase time interval for which the color developed during enzymatic reaction is preserved, to intensify the procedure of measuring cholesterol levels on skin and to widen the possibilities for urgent diagnosis of cholesterol.

According to a broad aspect of the present invention, there is provided a multilayer analytical element for determining a level of an analyte on substrate and adapted for use with hydrogen peroxide and an affinity-enzymatic compound of formula A-C-B, wherein A is a detecting agent having affinity for the ayalyte, B is an enzymatic visualizing agent consisting of peroxidase and C is a binding agent linking the detecting and visualizing agents together. The multilayer analytical element of the invention comprises a solid support and a hydrophilic layer thereon, the hydrophilic layer being formed of gelatin, polyvinyl alcohol or a mixture thereof and containing a developing agent and a hydrophobic color-producing agent in a total amount of 5 to 30 weight %, the developing agent and the color-producing agent being present in a weight ratio of 1:0.3 to 1:3.0. The developing agent is capable of undergoing oxidation by the hydrogen peroxide in the presence of the peroxidase bound via the binding and detecting agents to the analyte on the substrate, whereby the developing agent in oxidized form reacts with the color-producing agent to form a colored product having a color indicative of cholesterol level.

DESCRIPTION OF PREFERRED EMBODIMENTS

The developing agent used is preferably a compound of the formula:

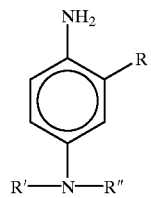

wherein R, R' and R" are identical or different and each represent a hydrogen atom, an alkyl or alkanol group having 1 to 5 carbon atoms, an alkenol group having 2 to 5 carbon atoms, a methylsulfonylaminoethyl group or a sulfopropyl group. Examples of such compounds include N,N-diethyl-paraphenylenediamine, para-ethylamino-orthotoluidine, para-[N-ethyl-N-(β-hydroxy-vinyl)amino]-aniline, para-[N-ethyl-N-(β-methylsulfonylaminoethyl)amino]-ortho-toluidine, para-[N-ethyl-N-(β-hydroxyethyl)amino]-orthotoluidine and para-[N-butyl-N-(γ-sulfopropyl)-amino]-aniline.

Use can also be made of diethyl-p-tolylenediamine, ethyloxyethyl-p-phenylenediamine, ethyl-methanesulfoaminoethyl-p-tolylenediamine, ethyloxy-ethyl-p-tolylenediamine, butylsulfopropyl-p-phenylene-diamine or diethyl-p-phenylenediamine as developing agent.

As color-producing agents, derivatives of pyrazolone-5, benzoylacetic acid or naphthoic acid can be used. Examples of suitable color-producing agents include 1-(2,4,6-trichlorophenyl)-3-pentadecylamino-phenyl-aminopyrazolone, 3,5-dicarboxyphenyloctadecylamide-1-oxy-2-naphthoic acid, 2-chloro-5-[γ-(2,4-ditetraminephenoxy)-butiroylamino]-anilide-α-N-benzoylhidantoylpivaloyl acetic acid, meta-(N-methyl-N-octadecyl)-amino-parabenzoylacetamidobenzenesulfonic acid, metacarboxy-meta-{N-[parachlorometa-(N-orthooctadecyl-oxybenzoylacetyl)amido]benzenesulfonylamido}-carboxylic acid, orthophenoxy-meta(5-oxo-1,2-pyrazol-3-ino)-benzenesulfonic acid, 2'-methyloctadecylamino-5'-sulfanilidebenzoylacetic acid, 2'-chloro-5'-(3",5"-dicarboxyphenylsulfamide)-anilide-2-octadecyloxybenzoylacetic acid, octadecylamide-1-oxy-4-sulfo-2-naphthoic acid, 2'-methyloctadecylamino-5'-sulfanilide-1,2-oxynaphthoic acid and 1-(4'-phenoxy-3'-sulfophenyl)-3-steroyl-aminopyrazolone.

The color-producing agents are evenly distributed in the hydrophilic layer as microcapsules, microparticles or separate molecules depending on the nature of color-producing agent. To achieve a micro-particular or molecular distribution of the color-producing agent in the hydrophilic layer, compounds with hydrophilic (polar) side chains are used. To achieve a microcapsular distribution of the color-producing agent, compounds with hydrophobic (nonpolar) side chains are used.

As a support, use is preferably made of a hydrophylized film of polyethyleneterephthalate, poly-ethylene or trinitro-cellulose. A noncolored polymer, paper or polyethylene-covered paper can also be used.

The hydrophilic layer can also contain moistening and tanning agents. Moistening agents ensure a uniform application on the support of a hydrophilic layer with a constant thickness, preferably of 2–100 microns. Tanning agents ensure the required level of physico-mechanical properties of the multilayer analytical element. Chrome acetate and the monosodium salt of 2,4-dichloro-6-hydroxytriazin-1,3,5 can be used as tanning agents.

The multilayer analytical element according to the invention can be used in medicine and pharmacology as well as in criminal law.

It is preferably utilized for determining level of cholesterol on human skin or other animal tissue. It can also be utilized for measuring chloride ions and glucose, thereby enabling the diagnosis of cysticfibrosis and diabetes.

The following non-limiting examples further illustrate the invention.

EXAMPLE 1

A multilayer analytical element for cholesterol assay in skin was produced by applying on a solid support consisting of a polyethyleneterephthalate film having a thickness of 50 microns, a layer of photographic gelatin containing 7.5 weight % of a hydrophobic purple color-producing agent consisting of 1-(2,4,6-trichlorophenyl)-3-pentadecyl-aminophenyl-amino-pyrazolone. The color-producing agent had an average particle size less than 0.1 micron. The gelatin layer contained 7.5 weight % of N,N-diethyl-paraphenylene-diamine as a developing agent distributed at molecular level. The layer also contained chrome acetate as a tanning agent.

This multilayer analytical element was used for the assay of cholesterol level on skin integument from the hand of a patient suffering from atherosclerosis as well as on the skin of a healthy person. One drop of an aqueous solution of an affinity-enzymatic compound of the formula A-C-B as defined above, in which the enzymatic visualizing agent B is a peroxidase, was applied on the skin of each person's palm. Incubation was performed for 1 minute, then the liquid was removed with the help of dry and moistened tampons alternately. In the same area, one drop of hydrogen peroxide was applied and immediately there-after the multilayer analytical element was placed firmly and pressed against the skin surface for 1 minute. The analytical element was then washed for 15–20 seconds in running water. The result of the assay was determined by comparing the color imprint obtained with a graduated scale or by measuring the intensity of color spot spectrophotometrically such as with a LCD (liquid crystal display) spectrophotometer.

Table 1 shows the results obtained by using known liquid-phase methods for measurement of blood and skin cholesterol levels as well as by using the multi-layer analytical element according to the invention.

TABLE 1

| Group | Known assay | | Present assay |
| | Blood cholesterol | Skin cholesterol | Skin Cholesterol |
| --- | --- | --- | --- |
| Healthy persons (24) | 185 ± 25 | 1.9 ± 0.3 | 0.13 ± 0.04 |
| Atherosclerotic patients (29) | 228 ± 32 | 2.8 ± 0.5 | 0.32 ± 0.07 |

The reproducibility of color reaction was studied on the same patients using 10 subsequent assays. The standard deviation was not higher than 8%.

Measurements performed using multilayer analytical elements which were stocked either for 1 week or for 6 months showed the same reproducibility of the results.

The assay took 2–3 minutes, and preparation of the assay took about 3 minutes. Kits for self-testing patients can thus be manufactured, incorporating the multilayer analytical element.

EXAMPLE 2

A multilayer analytical element for measuring cholesterol level on skin was produced by applying on a support consisting of a white polyethylene-covered photographic paper, a layer of polyvinyl alcohol containing a blue color-producing agent consisting of 3,5-dicarboxyphenyloctadecylamide-1-oxy-2-naftoic acid. The polyvinyl alcohol layer also contained para-ethylamino-orthotoluidine as a developing agent.

This multilayer analytical element was used for cholesterol assay on skin, according to the same procedure as described in Example 1. Essentially the same results were obtained.

EXAMPLE 3

A flexible multilayer analytical element was produced by applying on a support consisting of a poly-ethylene film with a thickness of 100 microns treated with plasma of corona discharge for its hydrophylization, a layer of gelatin in admixture with polyvinyl alcohol and containing a dispersion of a hydrophobic yellow color-producing agent, i.e. 2-chloro-50[γ-(2,4-ditetraminephenoxy)-butiroylamino]-anilide-α-N-benzoyl-hidantoylpivaloyl acetic acid. The layer of gelatin and polyvinyl alcohol also contained para-[N-ethyl-N-(β-hydroxyvinyl)amino]-aniline as a developing agent.

This multilayer analytical element was used for cholesterol assay on skin, according to the same procedure as described in Example 1. Essentially the same results were obtained.

What is claimed is:

1. A method of determining a level of an analyte on a solid surface comprising the steps of:
    providing a source of hydrogen peroxide;
    providing a source of an affinity-enzymatic compound of formula A-C-B, wherein A is a detecting agent having affinity for said analyte, B is an enzymatic visualizing agent consisting of peroxidase and C is a binding agent linking said detecting agent and said visualizing agent to one another;
    providing a multilayer analytical element comprising a solid support and a hydrophilic layer thereon, said hydrophilic layer being formed of gelatin, polyvinyl alcohol or a mixture thereof and containing a developing agent and a hydrophobic color-producing agent in a total amount of 5 to 30 weight % based on the weight of said hydrophilic layer, said developing agent and said color-producing agent being present in a weight ratio of 1:0.3 to 1:3.0;
    applying a predetermined amount of said affinity-enzymatic compound onto said surface in a selected area thereof and allowing said compound to stand thereon for a period of time sufficient to cause binding of said detecting agent to said analyte on said surface;
    removing any affinity-enzymatic compound with unbound detecting agent from said surface;
    applying a predetermined amount of hydrogen peroxide onto said surface in said selected area; and
    pressing said multilayer analytical element against said surface in said selected area;
    wherein said developing agent undergoes oxidation by the hydrogen peroxide in the presence of said peroxidase, bound via said binding and detecting agents to said analyte, and the developing agent in oxidized form reacts with said color-producing agent to form a colored product having a color indicative of the level of said analyte.

2. The method according to claim 1, wherein said developing agent is a compound of formula:

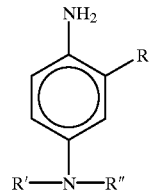

wherein R, $R^1$ and $R^{11}$ are identical or different and each represent a hydrogen atom, an alkyl or alkanol group having 1 to 5 carbon atoms, an alkenol group having 2 to 5 carbon atoms, a methylsulfonylaminoethyl group or a sulfopropyl group.

3. The method according to claim 1, wherein said developing agent is a compound selected from the group consisting of diethyl-p-tolylenediamine, ethyloxyethyl-p-phenylenediamine, ethylmethane-sulfoaminoethyl-p-tolylenediamine, ethyloxyethyl-p-tolylonediamine, butylsulfo-propyl-p-phenylenediamine and diethyl-p-phenylenediamine.

4. The method according to claim 1, wherein said color-producing agent is a compound selected from the group consisting of derivatives of pyrazolone-5, benzoylacetic acid and naphthoic acid.

5. The method according to claim 4, wherein said color-producing agent is a hydrophobic compound having a particle size less than 0.1 μm.

6. The method according to claim 1, wherein said hydrophilic layer has a thickness ranging from 2 to 100 μm.

7. The method according to claim 1, wherein said hydrophilic layer further contains at least one moistening agent.

8. The method according to claim 1, said hydrophilic layer further contains at least one tanning agent.

9. The method according to claim 1, wherein said analyte is cholesterol and said solid surface is a surface of an animal tissue.

10. The method according to claim 2, wherein said developing agent is a compound selected from the group consisting of N,N-diethyl-paraphenylenediamine, paraethylamino-orthotoluidine, para-[N-ethyl-N-(β-hydroxyvinyl)amino]-aniline, para-[N-ethyl-N-(β-methylsulfonylaminoethyl)amino]-orthotoluidine, para-[N-ethyl-N-(β-hydroxyethyl)amino]-orthotoluidine and para-[N-butyl-N-(γ-sulfopropyl)amino]-aniline.

11. The method according to claim 4, wherein said color-producing agent is a compound selected from the group consisting of 1-(2,4,6-trichlorophenyl)-3-pentadecylaminophenyl-amino-pyrazolone, 3,5-dicarboxyphenyloctadecylamide-1-oxy-2-naphthoic acid, 2-chloro-5-[γ-(2,4-ditetraminephenoxy)-butiroylamino]-anilide-α-N-benzoylhidantoylpivaloyl acetic acid, meta-(N-methyl-N-octadecyl)amino-parabenzoylacetamidobenzenesulfonic acid, metacarboxy-meta-{N-[parachlorometa-(N-orthooctadecyloxybenzoylacetyl)amido]benzensulfonylamido}-carboxylic acid, ortho-phenoxy-meta (5-oxo-1,2-pyrazol-3-ino)-benzenesulfonic acid, 2'-methyloctadecylamino-5'-sulfanilidebenzoylacetic acid, 2'-chloro-5'-(3",5"-dicarboxyphenylsulfamide)-anilide-2-octadecyloxybenzoylacetic acid, octa-decylamide-1-oxy-4-sulfo-2-naphthoic acid, 2'-methyl-octadecylamino-5'-sulfanilide-1,2-oxynaphthoic acid and 1-(4'-phenoxy-3'-sulfophenyl)-3-steroyl-aminopyrazolone.

12. The method according to claim 5, wherein said hydrophobic compound is 1-(2,4,6-trichlorophenyl)-3-pentadecylaminophenyl-aminopyrazolone or 2-chloro-5-[γ-(2,4-ditetraminephenoxy)-butiroylamino]-anilide-α-N-benzoylhidantoylpivaloyl acetic acid.

* * * * *

UNITED STATES PATENT AND TRADEMARK OFFICE
CERTIFICATE OF CORRECTION

PATENT NO. : 6,605,440 B2
DATED : August 12, 2003
INVENTOR(S) : Maleev et al.

It is certified that error appears in the above-identified patent and that said Letters Patent is hereby corrected as shown below:

<u>Title page,</u>
Item [*] Notice, "Subject to any disclaimer, the term of this patent is extended or adjusted under 35 U.S.C. 154(b) by 263 days." should read -- Subject to any disclaimer, the term of this patent is extended or adjusted under 35 U.S.C. 154(b) by 0 days. --

Signed and Sealed this

Thirteenth Day of July, 2004

JON W. DUDAS
*Acting Director of the United States Patent and Trademark Office*